United States Patent [19]

Sano et al.

[11] Patent Number: 5,516,919
[45] Date of Patent: May 14, 1996

[54] PROCESS FOR PRODUCING ASCORBIC ACID DERIVATIVE

[75] Inventors: Atsunori Sano; Kuniaki Okamoto; Jun Ebashi, all of Kawagoe, Japan

[73] Assignee: Wako Pure Chemical Industries, Ltd., Osaka, Japan

[21] Appl. No.: 423,988

[22] Filed: Apr. 18, 1995

[30] Foreign Application Priority Data

Apr. 28, 1994 [JP] Japan ................................ 6-113570

[51] Int. Cl.$^6$ .......................... C07F 9/655; C07D 307/62
[52] U.S. Cl. ............................ 549/222; 549/316; 549/317
[58] Field of Search ................................ 549/222, 316, 549/317

[56] References Cited

U.S. PATENT DOCUMENTS

| | | | |
|---|---|---|---|
| 4,070,377 | 1/1978 | Hayashi et al. | 549/317 |
| 4,071,534 | 1/1978 | Hayashi et al. | 549/317 |
| 4,724,262 | 2/1988 | Shimbo et al. | 549/222 |
| 5,118,817 | 6/1992 | Yoshida et al. | 549/222 |
| 5,212,079 | 5/1993 | Fujio et al. | 435/131 |

FOREIGN PATENT DOCUMENTS

| | | |
|---|---|---|
| 59-51293 | 3/1984 | Japan . |
| 59-106494 | 6/1984 | Japan . |
| 62-30791 | 2/1987 | Japan . |

OTHER PUBLICATIONS

Chemical Abstracts vol. 86–95999 (1976); abstract of Spanish ES 425,881, Jul. 1, 1976.
Nomura et al., Chem. Pharm. Bull., 17(2), pp. 381–386 (1969).
Derwent Publication—Abstract of JP A 63–077890 (1988).
Derwent Publication—Abstract of JP A 62–103096 (1987).
Derwent Publication—Abstract of JP B 84–4438 (1984).
Derwent Publication—Abstract of JP B 68–9219 (1968).
Derwent Publication—Abstract of JP A 51–11757 (1976).
Derwent Publication—Abstract of JP A 50–59363 (1975).

*Primary Examiner*—Bernard Dentz
*Attorney, Agent, or Firm*—Armstrong, Westerman, Hattori, McLeland & Naughton

[57] ABSTRACT

Metal salts or substitutted or non-substituted ammonium salts of ascorbic acid derivatives can be produced in high yield by treating an acidic aqueous solution containing ascorbic acid-2-phosphate or ascorbic acid-2-sulfate with a porous adsorbent such as activated carbon, followed by treating the adsorbent with a basic aqueous solution containing e.g. a metal salt of an organic acid or substituted or non-substituted ammonium salt ion to elute the desired salt of ascorbic acid derivative.

12 Claims, No Drawings

PROCESS FOR PRODUCING ASCORBIC ACID DERIVATIVE

BACKGROUND OF THE INVENTION

The present invention relates to process for production of ascorbic acid-2-phosphate salts and ascorbic acid-2-sulfate salts, such as magnesium ascorbic acid-2-phosphate, sodium ascorbic acid-2-sulfate, etc., which are widely used as, for example, stable ascorbic acid derivatives in the fields of cosmetics, foods, medicines, etc.

In the fields of cosmetics, foods, etc., ascorbic acid-2-phosphate and ascorbic acid-2-sulfate are used usually in the form of metal salts. Particularly when they are used in the field of cosmetics, they are required to be of high quality. Therefore, various production processes and purification processes of metal salts of ascorbic acid derivatives have been reported.

For example, JP-A 59-106494 discloses a process comprising decoloring an aqueous solution of ascorbic acid phosphate or a salt thereof with activated carbon, diatomaceous earth, acid clay or the like by adsorbing coloring components, and subjecting the thus treated solution to crystallization from a lower alcohol, a ketone or the like to obtain a desired compound.

JP-A 59-51293 discloses a process comprising adsorbing an acidic aqueous solution of L-ascorbic acid-2-phosphate on activated carbon packed in a column, eluting the phosphate with an aqueous solvent such as a water-soluble organic solvent (e.g. methanol) or an aqueous solution of a basic substance (e.g. sodium hydroxide) to purify the same, and then obtaining the salt of the phosphate.

JP-A 62-30791(=U.S. Pat. No. 4,724,262) discloses a process comprising treating an aqueous solution of L-ascorbic acid-2-phosphate with a weakly or moderately basic ion-exchange resin column to adsorb the phosphate, followed by elution with a mineral acid or an inorganic salt (neutral).

In JP-A 59-51293 among the above processes, the adsorbate is eluted with an aqueous solution of a basic substance, but no invention idea of obtaining a desired metal salt directly is disclosed at all.

On the other hand, production processes of metal salts of ascorbic acid-2-phosphate have also been reported (for example, JP-B 43-9219, JP-B 59-4438, JP-A 1-199590 (=U.S. Pat. No. 5,212,079), JP-A 3-204891 (U.S. Pat. No. 5,118,817), and those of metal salts of ascorbic acid-2-sulfate have also been reported (for example, JP-B 57-52344 (U.S. Pat. No. 4,070,377 and U.S. Pat. No. 4,071,534), JP-A 50-59363, JP-A 51-11757, etc.).

In all of the production processes disclosed in these references, steps "phosphorylation or sulfation→deionization→salt formation→separation" are generally carried out, and a purification process using activated carbon, an ion exchange resin, a chelating resin or the like is added after the deionization or the salt formation in order to obtain a product of high quality.

When a salt of ascorbic acid-2-phosphate or ascorbic acid-2-sulfate is used in the field of cosmetics, the salt is required to be a high-quality one which is colorless and odorless and has high solubility, stability and purity. For assuring the high quality, it is unavoidable to employ a complicated production or purification process, though the salt is a relatively simple compound.

That is, even if the yield from reaction is increased by improving a reaction method and reaction conditions, there is still a problem, for example, in that deionization, purification and salt formation steps after the reaction are complicated, require a long period of time, and cause an yield decrease.

In order to solve such problems, a production process by electrodialysis has been reported (JP-A 63-77890), but it requires a special electrodialysis apparatus and a technical skill and entails high cost. Moreover, since mere purification by electrodialysis gives an insufficient purity, it is necessary to employ together therewith a conventional method comprising cation elimination with an ion exchange resin, followed by salt formation. Thus, the problems have not yet been sufficiently solved.

SUMMARY OF THE INVENTION

The present invention is intended to provide an effective process for producing an ascorbic acid-2-phosphate salt or an ascorbic acid-2-sulfate salt which makes it possible to obtain a product of high quality in high yield by simple and easy operations.

The present invention provides a process for producing a metal salt or substituted ammonium salt of ascorbic acid-2-phosphate, which comprises treating an acidic aqueous solution containing ascorbic acid-2-phosphate with a porous adsorbent to adsorb said ascorbic acid-2-phosphate, and treating the adsorbent with a basic aqueous solution of an alkali metal, alkaline earth metal, aluminum or zinc salt of organic acid, or substituted ammonium ions selected from the group consisting of cycloalkylamine ions and cyclic amine ions to elute the metal salt or substituted ammonium salt of ascorbic acid-2-phosphate.

The present invention also provides a process for producing a metal salt or substituted or non-substituted ammonium salt of ascorbic acid-2-sulfate, which comprises treating an acidic aqueous solution containing ascorbic acid-2-sulfate with a porous adsorbent to adsorb said ascorbic acid-2-sulfate, and treating the adsorbent with a basic aqueous solution containing metal ions or substituted or non-substituted ammonium ions to elute the metal salt or substituted or non-substituted ammonium salt of ascorbic acid-2-sulfate.

DESCRIPTION OF THE PREFERRED EMBODIMENTS

In order to solve the problems described above, the present inventors earnestly investigated a process for producing an ascorbic acid-2-phosphate salt or an ascorbic acid-2-sulfate salt, in particular, after-treatment step in the process, and consequently found that a very efficient production process in which the steps of deionization, purification and salt formation in conventional processes have been simplified. Thus, the present invention has been accomplished.

In detail, when an acidic aqueous solution containing ascorbic acid-2-phosphate or ascorbic acid-2-sulfate (these compounds are hereinafter abbreviated as "starting material" in some cases) (the acidic aqueous solution is hereinafter abbreviated as "starting solution for adsorption") is treated with a porous adsorbent, the starting material is adsorbed but by-products such as inorganic substances and other impurities which are present in the starting solution for adsorption are not adsorbed and can be removed. When elution is then carried out using a basic eluent containing metal ions or substituted or non-substituted ammonium ions, which are necessary for forming a desired ascorbic acid-2-phosphate or ascorbic acid-2-sulfate salt, the ascorbic acid-2-phosphate or ascorbic acid-2-sulfate salt of high quality can be eluted without elution of impurities such as coloring components.

The starting solution for adsorption used can be prepared by distilling off the solvent from a reaction solution obtained by a conventional process, for example, any of the processes disclosed in JP-A 1-199590 (=U.S. Pat. No. 5,212,079), JP-A 3-204891 (=U.S. Pat. No. 5,118,817), JP-B 57-52344 (=U.S. Pat. No. 4,070,377), etc. and other processes if necessary, or filtering the reaction solution if necessary, and adding an acid such as hydrochloric acid, sulfuric acid or acetic acid to the residue. The starting solution for adsorption can be prepared also by dissolving a salt of ascorbic acid-2-phosphate or ascorbic acid-2-sulfate obtained by an optional method, in an acid such as hydrochloric acid, sulfuric acid or acetic acid. It is sufficient that the starting solution for adsorption is acidic to such an extent that ascorbic acid-2-phosphate or ascorbic acid-2-sulfate can exist in a free form. The pH of the starting solution for adsorption is preferably 3 or lower.

The adsorption treatment may be carried out by a conventional method using an adsorbent. A simple, efficient and preferable adsorption method is, for example, column treatment in which a column is packed with an adsorbent and the starting solution for adsorption is passed through the column to effect adsorption. Needless to say, there may also be employed batch treatment in which an adsorbent is added to the starting solution for adsorption and stirred to effect adsorption.

As the porous adsorbent used, packings usually used in the fields of column chromatography, etc. can be exemplified, and any porous adsorbent may be used so long as it is porous powder or a porous and granular solid, which has a large surface area, adsorb the starting material and is insoluble in water and solvents. There can be exemplified inorganic porous materials such as activated carbon, diatomaceous earth, silica gel, etc.; natural polymers such as dextran, agarose, etc.; and synthetic polymers such as polyacrylamides, hydrophilic vinyl polymers, polystyrenes, etc. Of these porous adsorbents, activated carbon such as granular activated carbon or ground activated carbon is particularly preferably used.

The adsorption conditions such as the amount of the adsorbent, the concentration of the starting solution for adsorption, the adsorption temperature, the shape of the column, the passage rate of the starting solution for adsorption, etc. are preferably properly determined so as to reduce the amount of non-adsorbed starting material as much as possible. Examples of preferable adsorption conditions are as follows. The amount of the adsorbent is about 1 to about 500 times, preferably about 2 to about 100 times, particularly preferably about 5 to about 40 times, as large as the amount of the starting material. The starting solution for adsorption may have any concentration so long as substances contained therein such as inorganic substances are dissolved, and it is preferably a dilute solution having a concentration of 5% or less. The adsorption temperature is preferably a relatively low temperature in the range of room temperature to about −10° C. The passage rate may be optionally determined.

After the adsorption, the solution passed through the column contains inorganic substances mainly, and the degree of removal of the inorganic substances can be monitored by means of electric conductivity. If the removal is not sufficient, the inorganic substances can be completely removed by passing a dilute solution of hydrochloric acid, sulfuric acid, acetic acid or the like through the column after the adsorption.

Next, there is explained below a method for eluting the starting material adsorbed on the adsorbent while making the starting material into a salt.

In the case of producing a metal salt or substituted ammonium salt of ascorbic acid-2-phosphate, an adsorbent adsorbing ascorbic acid-2-phosphate is treated with a basic aqueous solution of an alkali metal, alkaline earth metal, aluminum or zinc salt of organic acid, or a substituted ammonium ions selected from the group consisting of cycloalkylammonium ions and cyclic ammonium ions to elute the metal salt or substituted ammonium salt of ascorbic acid-2-phosphate.

In the case of eluting the desired ascorbic acid-2-phosphate salt directly, for example, in the form of magnesium ascorbic acid-2-phosphate directly, a basic aqueous solution containing magnesium ions is used as an eluent for the elution. Specific examples of such an eluent are eluents containing metal ions, for instance, aqueous solutions containing any of alkali metal salts of organic acids (e.g. lithium acetate, lithium carbonate, sodium acetate, sodium carbonate, potassium acetate, potassium carbonate, etc.), aqueous solutions containing any of alkaline earth metal salts of organic acids (e.g. magnesium acetate, calcium acetate, etc.), and aqueous solutions containing any of metal salts such as aluminum acetate, zinc carbonate, etc.; and basic aqueous solutions containing substituted ammonium ions, for instance, aqueous solutions containing any of amines such as cycloalkylamine having 3 to 8 carbon atoms (e.g. cyclopropylamine, cyclohexylamine, cyclooctyl-amine, etc.) and cyclic amines (e.g. morpholine, piperidine, piperazine, etc.).

By using a mixture of two or more of these eluents, a corresponding mixed salt can be obtained.

Although the eluent is usually an aqueous solution, a solution in a mixture of water and a water-soluble solvent such as methanol, ethanol, propanol, acetone or the like may also be used if necessary. The elution conditions such as the concentration of the eluent, the volume of the eluent used, the elution temperature, the shape of the column, the passage rate of the eluent, etc. are preferably properly determined so that the starting material can be eluted rapidly in high yield. Examples of preferable elution conditions are as follows. Although optional, the concentration of the eluent is preferably 10% or less. If necessary, the eluent can be used while being varied stepwise in concentration. Although the elution temperature may be any temperature so long as it does not affect the quality of the resulting eluate, it is preferably about 0° C. to about 60° C., particularly preferably room temperature to about 40° C. The passage rate of the eluent is not critical and may be determined in view of the operation time, though for example, when the passage rate is the same as the flow rate employed at the time of adsorption, there are advantages such as simplification of operations. Since the eluate is a solution containing the desired component, monitoring of the eluate is important. The monitoring can easily be carried out by continuous measurement of the absorbance and refractive index of the eluate. In this point, the column method is preferable to the batch method.

In the case of producing a metal salt or substituted or non-substituted ammonium salt of ascorbic acid-2-sulfate, the porous adsorbent adsorbing the ascorbic acid-2-sulfate is treated with a basic aqueous solution containing metal ions or substituted or non-substituted ammonium ions to elute the metal salt or substituted or non-substituted ammonium salt of ascorbic acid-2-sulfate.

In further detail, as an eluent used for the elution, there is used a basic aqueous solution containing metal ions or substituted or non-substituted ammonium ions, which correspond to the salt moiety of the desired ascorbic acid-2-sulfate salt (for example, an aqueous solution containing magnesium ions is used in the case where the ascorbic acid-2-sulfate adsorbed is to be eluted to give magnesium ascorbic acid-2-sulfate directly). Specific examples of such an eluent are eluents containing metal ions, for instance, aqueous solutions containing any of alkali metal salts of organic acids (e.g. lithium acetate, sodium acetate, sodium carbonate, potassium acetate, potassium carbonate, etc.), aqueous solutions containing any of alkali metal phosphates (e.g. sodium phosphate, potassium phosphates, etc.), aqueous solutions containing any of alkali metal hydroxides (e.g. lithium hydroxide, sodium hydroxide, potassium hydroxide, etc.), aqueous solutions containing any of alkaline earth metal salts of organic acids (e.g. magnesium acetate, calcium acetate, etc.), and aqueous solutions containing any of metal salts such as aluminum acetate, zinc carbonate, etc.; and basic aqueous solutions containing substituted or non-substituted ammonium ions, for instance, aqueous ammonia and aqueous solutions containing any of amines such as methylamine, ethylamine, cycloalkylamine having 3 to 8 carbon atoms (e.g. cyclopropylamine, cyclohexylamine, cyclooctylamine, etc.) and cyclic amines (e.g. morpholine, piperidine, piperazine, etc.).

By using a mixture of two or more of these eluents, a corresponding mixed salt can be obtained.

Although the eluent is usually an aqueous solution, a solution in a mixture of water and a water-soluble solvent such as methanol, ethanol, propanol, acetone or the like may also be used if necessary. The elution conditions such as the concentration of the eluent, the volume of the eluent used, the elution temperature, the shape of the column, the passage rate of the eluent, etc. are preferably properly determined so that the starting material can be eluted rapidly in high yield. Examples of preferable elution conditions are as follows. Although optional, the concentration of the eluent is preferably 10% or less. If necessary, the eluent can be used while being varied stepwise in concentration. Although the elution temperature may be any temperature so long as it does not affect the quality of the resulting eluate, it is preferably about 0° C. to about 60° C., particularly preferably room temperature to about 40° C. The passage rate of the eluent is not critical and may be determined in view of the operation time, though for example, when the passage rate is the same as the flow rate employed at the time of adsorption, there are advantages such as simplification of operations. Since the eluate is a solution containing the desired component, monitoring of the eluate is important. The monitoring can easily be carried out by continuous measurement of the absorbance and refractive index of the eluate. In this point, the column method is preferable to the batch method.

In any of the elution steps described above, impurities such as coloring components which are produced in the reaction step are kept adsorbed and are not eluted, so that they can be separated. Therefore, a solution of an ascorbic acid-2-phosphate or ascorbic acid-2-sulfate salt of high quality can be obtained. For isolating the ascorbic acid-2-phosphate or ascorbic acid-2-sulfate salt from this solution, a solvent incapable of dissolving the desired ascorbic acid-2-phosphate or ascorbic acid-2-sulfate salt, for example, a water-soluble solvent such as methanol, ethanol, propanol, acetone or the like is added to the obtained solution after concentrating the solution if necessary, to precipitate the ascorbic acid-2-phosphate or ascorbic acid-2-sulfate salt as an insoluble substance, and the insoluble substance is isolated by a method such as filtration, centrifugation or the like.

Thus, according to the process of the present invention, coloring and deterioration of the ascorbic acid-2-phosphate or ascorbic acid-2-sulfate salt during purification can be prevented as much as possible.

For example, when ascorbic acid-2-phosphate or ascorbic acid-2-sulfate is made into magnesium salt, conventional processes are disadvantageous in that since they use difficultly water-soluble magnesium oxide as a salt-forming agent, the final product is contaminated with the surplus magnesium oxide to be deteriorated in quality. In the present invention, since water-soluble magnesium is used as a salt-forming agent corresponding to the magnesium salt, the above disadvantage is removed.

Furthermore, according to the process of the present invention, conventional steps of deionization, purification and salt formation can be gathered into one run of conventional column chromatography operation, so that an ascorbic acid-2-phosphate or ascorbic acid-2-sulfate salt of high quality can easily be obtained by a very simple procedure.

Typical and specific examples of the ascorbic acid-2-phosphate salt obtained by the process of the present invention are magnesium L-ascorbic acid-2-phosphate, potassium L-ascorbic acid-2-phosphate, sodium L-ascorbic acid-2-phosphate, cyclohexylammonium L-ascorbic acid-2-phosphate, magnesium potassium L-ascorbic acid-2-phosphate, magnesium sodium L-ascorbic acid-2-phosphate, etc. The ascorbic acid-2-phosphate salt is not limited to these compounds.

Typical and specific examples of the ascorbic acid-2-sulfate salt obtained by the process of the present invention are magnesium L-ascorbic acid-2-sulfate, potassium L-ascorbic acid-2-sulfate, sodium L-ascorbic acid-2-sulfate, cyclohexylammonium L-ascorbic-acid-2-sulfate, magnesium potassium L-ascorbic acid-2-sulfate, magnesium sodium L-ascorbic acid-2-sulfate, etc. Needless to say, the ascorbic acid-2-sulfate salt is not limited to these compounds.

The present invention is illustrated below in further detail with reference to Examples, which are not by way of limitation but by way of illustration.

EXAMPLE 1

A solution consisting of 52.8 g of L-ascorbic acid, 965 ml of water and 37 ml of pyridine was cooled to 0°–5° C., and 71 g of phosphoryl chloride was added dropwise with stirring over a period of about 2 hours while maintaining the pH at 12.7±0.2 with a 50% aqueous potassium hydroxide solution. After completion of the dropwise addition, the resulting mixture was stirred at the same temperature for about 30 minutes. After completion of the reaction, the pyridine was distilled off under reduced pressure at about 40° C., and the residue was adjusted to a pH of about 1 with concentrated hydrochloric acid and then diluted with water to adjust the L-ascorbic acid-2-phosphate concentration to about 2%, whereby a starting solution for adsorption was prepared. The starting solution for adsorption was cooled to 0°–5° C. and passed through a column of activated carbon cooled to 0°–5° C. [a column with a diameter of 10 cm and a length of 30 cm which had been packed with activated carbon (Ryujo Shirasagi, mfd. by Takeda Chemical Industries, Ltd.) by a wet process so that the length of packed portion of the column might be 20 cm] at a flow rate SV=1 to be subjected to adsorption. Then, a 0.5% aqueous hydrochloric acid solution was passed through the column under the same conditions as above until the electric conductivity of the solution became 20 ms or less. Subsequently, a 2% aqueous magnesium acetate solution was passed through the column at a flow rate SV=1 at room temperature to elute a desired component (magnesium L-ascorbic acid-2-phosphate). The eluate thus obtained was monitored by means of absorbance and a fraction containing 0.1% or more of the desired component was separated therefrom as an available fraction. The available fraction was concentrated to adjust the concentration of the desired component to about 10%, after which acetone was added in a volume of twice that of the residue with stirring to precipitate magnesium L-ascorbic acid-2-phosphate. The crystals precipitated were collected by filtration and then dried by air blowing at room temperature to obtain 65 g of magnesium L-ascorbic acid-2-phosphate. The magnesium L-ascorbic acid-2-phosphate obtained had a purity of as good as 98% (in terms of dehydrate) and an absorbance of as good as 0.01 or less (360 nm, C=1%).

EXAMPLE 2

Treatment was carried out in exactly the same manner as described in Example 1 except for using a 3% aqueous potassium acetate solution as eluent in place of the 2% aqueous magnesium acetate solution, to obtain 54 g of potassium L-ascorbic acid-2-phosphate. The potassium L-ascorbic acid-2-phosphate obtained had a purity of as good as 97% (in terms of dehydrate) and an absorbance of as good as 0.01 or less (430 nm, C=1%).

EXAMPLE 3

Treatment was carried out in exactly the same manner as described in Example 1 except for using a 2% aqueous sodium carbonate solution as eluent in place of the 2% aqueous magnesium acetate solution, to obtain 71 g of sodium L-ascorbic acid-2-phosphate. The sodium L-ascorbic acid-2-phosphate obtained had a purity of as good as 97% (in terms of dehydrate) and an absorbance of as good as 0.01 or less (430 nm, C=1%).

EXAMPLE 4

Column treatment was carried out in exactly the same manner as described in Example 1 except for using a 2% aqueous cyclohexylamine solution as eluent in place of the 2% aqueous magnesium acetate solution, to obtain a tricyclohexylammonium L-ascorbic acid-2-phosphate solution. This solution was concentrated under reduced pressure and the residue was recrystallized three times from ethanol to obtain 52 g of crystals of tricyclo-hexylammonium L-ascorbic acid-2-phosphate. The crystals had a purity of as good as 99.5% and an absorbance of as good as 0.01 or less (430 nm, C=1%).

EXAMPLE 5

To a solution consisting of 10 g of 5,6-isopropylidene-L-ascorbic acid, 20 ml of dimethylformamide and 4 ml of pyridine was added dropwise 40 ml of a solution of 14 g of pyridine-sulfur trioxide complex in dimethylformamide with stirring at room temperature. The resulting mixture was stirred for 24 hours, after which 60 ml of water was added to the reaction solution and the solvent was distilled off under reduced pressure. The residue was adjusted to a pH of about 1 with concentrated hydrochloric acid and then diluted with water to adjust the L-ascorbic acid-2-sulfate concentration to about 2%, and the dilution was stirred at room temperature for 1 hour to obtain a starting solution for adsorption. The starting solution for adsorption was cooled to 0°–5° C. and passed through a column of activated carbon cooled to 0°–5° C. [a column with a diameter of 3 cm and a length of 30 cm which had been packed with activated carbon (Ryujo Shirasagi, mfd. by Takeda Chemical Industries, Ltd.) by a wet process so that the length of packed portion of the column might be 20 cm] at a flow rate SV=1 to be subjected to adsorption. Then, a 0.5% aqueous hydrochloric acid solution was passed through the column under the same conditions as above until the electric conductivity of the solution became 20 ms or less. Subsequently, a 1% aqueous sodium hydroxide solution was passed through the column at a flow rate SV=1 at room temperature to elute a desired component (sodium L-ascorbic acid-2-sulfate). The eluate thus obtained was monitored by means of absorbance and a fraction containing 0.1% or more of the desired component was separated therefrom as an available fraction. The available fraction was concentrated to adjust the concentration of the desired component to about 10%, after which acetone was added in a volume of three times that of the residue with stirring to precipitate sodium L-ascorbic acid-2-sulfate. The crystals precipitated were collected by filtration and then dried by air blowing at room temperature to obtain 16 g of sodium L-ascorbic acid-2-sulfate. The sodium L-ascorbic acid-2-sulfate obtained had a purity of as good as 95% (in terms of dehydrate) and an absorbance of as good as 0.01 or less (430 nm, C=1%).

According to the processes of the present invention, ascorbic acid-2-phosphate salts of high quality and ascorbic acid-2-sulfate salts of high quality can be obtained easily in high yield. Therefore, the processes of the present invention permit industrial-scale production of the ascorbic acid-2-phosphate salts and the ascorbic acid-2-sulfate salts.

What is claimed is:

1. A process for producing a metal salt or substituted ammonium salt of ascorbic acid-2-phosphate, which comprises treating an acidic aqueous solution containing ascorbic acid-2-phosphate with a porous adsorbent to adsorb said ascorbic acid-2-phosphate, treating the adsorbent with a basic aqueous solution of an alkali metal, alkaline earth metal, aluminum or zinc salt of an organic acid, or substituted ammonium ions selected from the group consisting of cycloalkylammonium ions and cyclic ammonium ions to elute the corresponding metal salt or substituted ammonium salt of ascorbic acid-2-phosphate, and isolating said metal salt or substituted ammonium salt of ascorbic acid-2-phosphate.

2. A process according to claim 1, wherein the porous adsorbent is activated carbon.

3. A process according to claim 1, wherein the alkali metal salt of organic acid in the basic aqueous solution is sodium acetate, potassium acetate, lithium acetate, sodium carbonate or potassium carbonate.

4. A process according to claim 1, wherein the alkaline earth metal salt of organic acid in the basic aqueous solution is magnesium acetate or calcium acetate.

5. A process according to claim 1, wherein the cycloalkylammonium ion in the basic aqueous solution is cyclohexylammonium ion.

6. A process for producing a metal salt or substituted ammonium salt of ascorbic acid-2-sulfate, which comprises treating an acidic aqueous solution containing ascorbic acid-2-sulfate with a porous adsorbent to adsorb said ascorbic acid-2-sulfate, treating the adsorbent with a basic aqueous solution containing metal ions or substituted or non-substituted ammonium ions to elute the corresponding metal salt or substituted or non-substituted ammonium salt of ascorbic acid-2-sulfate.

7. A process according to claim 6, wherein the porous adsorbent is activated carbon.

8. A process according to claim 6, wherein the basic aqueous solution contains lithium acetate, sodium acetate, sodium carbonate, sodium phosphate, potassium acetate, potassium carbonate, potassium phosphate, lithium hydroxide, sodium hydroxide, or potassium hydroxide.

9. A process according to claim 6, wherein the basic aqueous solution contains magnesium acetate, calcium acetate, aluminum acetate or zinc carbonate.

10. A process according to claim 6, wherein the basic aqueous solution contains ammonia, methylamine, ethylamine, cyclohexylamine, or morpholine.

11. A process according to claim 1, wherein the metal salt of ascorbic acid-2-phosphate is magnesium ascorbic acid-2-phosphate.

12. The process according to claim 6, wherein the metal salt of ascorbic acid-2-sulfate is sodium ascorbic acid-2-sulfate.

\* \* \* \* \*